(12) United States Patent
Korn

(10) Patent No.: US 10,332,634 B2
(45) Date of Patent: Jun. 25, 2019

(54) SYSTEMS AND METHODS FOR RELIABLY DIAGNOSING BREAST CANCER USING QUANTITATIVE TEXTURAL ANALYSIS

(71) Applicant: Imaging Endpoints II LLC, Scottsdale, AZ (US)

(72) Inventor: Ronald L. Korn, Paradise Valley, AZ (US)

(73) Assignee: Imaging Endpoints II LLC, Scottsdale, AZ (US)

( * ) Notice: Subject to any disclaimer, the term of this patent is extended or adjusted under 35 U.S.C. 154(b) by 0 days.

(21) Appl. No.: 15/458,232

(22) Filed: Mar. 14, 2017

(65) Prior Publication Data
US 2018/0268107 A1    Sep. 20, 2018

(51) Int. Cl.
| | |
|---|---|
| G06K 9/00 | (2006.01) |
| G16H 50/20 | (2018.01) |
| A61B 5/00 | (2006.01) |
| G06T 7/00 | (2017.01) |
| G06T 7/44 | (2017.01) |
| A61B 6/00 | (2006.01) |
| A61B 8/08 | (2006.01) |
| A61B 5/055 | (2006.01) |

(52) U.S. Cl.
CPC ........... *G16H 50/20* (2018.01); *A61B 5/4312* (2013.01); *A61B 5/7275* (2013.01); *A61B 5/743* (2013.01); *A61B 5/748* (2013.01); *A61B 5/7435* (2013.01); *G06T 7/0012* (2013.01); *G06T 7/44* (2017.01); *A61B 5/055* (2013.01); *A61B 6/5217* (2013.01); *A61B 8/5223* (2013.01); *A61B 2576/00* (2013.01); *G06T 2207/10072* (2013.01); *G06T 2207/30068* (2013.01); *G06T 2207/30096* (2013.01)

(58) Field of Classification Search
CPC ... A61B 2576/00; A61B 5/055; A61B 5/4312; A61B 5/7275; A61B 5/743; A61B 5/7435; A61B 5/748; A61B 6/5217; A61B 8/5223; G06T 2207/30068; G06T 2207/30096; G06T 7/0014; G06T 7/41; G16H 50/20
See application file for complete search history.

(56) References Cited

U.S. PATENT DOCUMENTS

| | | | |
|---|---|---|---|
| 7,769,423 | B2 | 8/2010 | Vigliant et al. |
| 9,092,691 | B1 * | 7/2015 | Beaumont ............. G06T 7/0014 |
| 9,304,973 | B2 | 4/2016 | Heine et al. |

(Continued)

FOREIGN PATENT DOCUMENTS

| | | |
|---|---|---|
| WO | 2012/125411 | 9/2012 |
| WO | 2014/097124 | 6/2014 |

OTHER PUBLICATIONS

Ganeshan et al ("Non-Small Cell Lung Cancer: Histopathologic Correlates for TextureParameters at CT", 2013).*

(Continued)

*Primary Examiner* — Avinash Yentrapati
(74) *Attorney, Agent, or Firm* — Jennings, Strouss & Salmon, PLC; Michael K. Kelly; Daniel R. Pote

(57) ABSTRACT

Methods and apparatus for using a biomarker signature to determine whether a breast tumor is malignant by comparing imaging data for the breast tumor to the signature, the signature derived using Quantitative Textural Analysis (QTA) and expressed in the form: Y=XCx+B; where: Y is a predictive indicator ranging from 0 to 1; B is a constant; Cx is a coefficient; and X is the mean positive pixel (MPP) value associated with the breast tumor under inspection.

7 Claims, 7 Drawing Sheets

(56) References Cited

U.S. PATENT DOCUMENTS

| | | | | |
|---|---|---|---|---|
| 2004/0258310 | A1* | 12/2004 | Giger | G06T 7/0012 |
| | | | | 382/190 |
| 2010/0142775 | A1* | 6/2010 | Ganeshan | G06K 9/4609 |
| | | | | 382/128 |
| 2010/0266179 | A1* | 10/2010 | Ramsay | G06T 7/0012 |
| | | | | 382/131 |
| 2013/0272595 | A1* | 10/2013 | Heine | A61B 5/4312 |
| | | | | 382/132 |
| 2014/0233826 | A1* | 8/2014 | Agaian | G16H 50/30 |
| | | | | 382/133 |
| 2015/0356730 | A1* | 12/2015 | Grove | G01N 23/046 |
| | | | | 382/124 |
| 2017/0119334 | A1* | 5/2017 | Smith | G06T 7/0016 |

OTHER PUBLICATIONS

Ganeshan et al ("Tumour heterogeneity in oesophageal cancer assessed by CT texture analysis: Preliminary evidence of an association with tumour metabolism, stage, and survival", 2012).*

Ng et al. ("Assessment of Primary Colorectal Cancer Heterogeneity by Using Whole-Tumor Texture Analysis: Contrast-enhanced CT Texture as a Biomarker of 5-year Survival1", 2013).*

Davnall et al. ("Assessment of tumor heterogeneity: an emerging imaging tool for clinical practice", 2012).*

Hopp, Alix. Effectiveness of using texture analysis in evaluating heterogeneity in breast tumor and in predicting tumor aggressiveness in breast cancer patients. Diss. The University of Arizona., 2016.*

Miles, Kenneth A., Balaji Ganeshan, and Michael P. Hayball. "CT texture analysis using the filtration-histogram method: what do the measurements mean?." Cancer Imaging 13.3 (2013): 400.*

De Cecco et al., "Texture analysis as imaging bIomarker of tumoral response to neoadjuvant chemoradiotherapy in rectal cancer patients studied with 3-T magnetic resonance," Investigate Radiology, Apr. 30, 2015 (Apr. 30, 2015), vol. 50, No. 4, pp. 239-245.

International Search Report, PCT/US17/47026; dated Nov. 22, 2017; 3 pgs.

Written Opinion, PCT/US17/47026; dated Nov. 22, 2017; 9 pgs.

* cited by examiner

300B

| Dependent Y | T_N Tumor |
| --- | --- |
| | t/N Tumor |

Least square multiple regression

| Method | Forward |
| --- | --- |
| Feed variable if Pc | 0.05 |
| Remove variable if Pc | 0.1 |

| Sample size | 40 |
| --- | --- |
| Coefficient of determination $R^2$ | 0.1159 |
| $R^2$ adjusted | 0.09263 |
| Multiple concession coefficient | 0.3404 |
| Residual around and deviation | 0.4823 |

Regression equation

| Independent variables | Coefficient | Std. Error | Number | t | P | VIP |
| --- | --- | --- | --- | --- | --- | --- |
| (Constant) | 0.8466 | | | | | |
| mpp_Tumor | -0.0005002 | 0.0002241 | 0.3404 | -2.232 | 0.0316 | 1000 |

Variables not included in the model

Portions_Tumor
entropy_Tumor
means_Tumor
sd_Tumor
skeptics_Tumor
Analysis of Variable

| Source | DF | Sum of Squares | Mean Squares |
| --- | --- | --- | --- |
| Regression | 1 | 1.1559 | 1.1509 |
| Residual | 36 | 3.2111 | 0.2327 |

| Rising | 1.90E2 |
| --- | --- |
| Significance Level | P×0.0315 |

Zero order and simple correlation coefficient

| Variable | T_N_Tumor | skeptics_Tumor | entropy_Tumor | mean_Tumor | mpp_Tumor | sd_Tumor |
| --- | --- | --- | --- | --- | --- | --- |
| Portions_Tumor | 0.3114 | | | | | |
| entropy_Tumor | -0.1149 | -0.1567 | | | | |
| mean_Tumor | -0.2195 | -0.001789 | -0.01941 | | | |
| mpp_Tumor | -0.3404 | -0.2226 | 0.4367 | 0.7645 | | |
| sd_Tumor | -0.2254 | -0.2356 | 0.7065 | 0.2917 | 0.8191 | |
| skeptics_Tumor | -0.08612 | 0.1929 | 0.07756 | -0.1229 | -0.09274 | -0.04176 |

FIG. 3B

| Variable | MPP |
|---|---|
| Classification variable | ER_status<br>ER status |

| Sample size | 36 |
|---|---|
| Positive group: ER status = 1 | 29 |
| Negative group: ER status = 0 | 7 |

| Disease prevalence (%) | unknown |
|---|---|

Area under the ROC curve (AUC)

| Area under the ROC curve (AUC) | 0.764 |
|---|---|
| Standard Error[a] | 0.112 |
| 95% Confidence interval[b] | 0.593 to 0.889 |
| z statistic | 2.362 |
| Significance level P (Area=0.5) | 0.0182 |

[a]DeLong et aL. 1988
[b]Binomial exact

Youden index

| Youden index J | 0.5813 |
|---|---|
| 95% Confidence interval[a] | 0.2759 to 0.7931 |
| Associated criterion | ≤14 |
| 95% Confidence interval[a] | 7.44 to 16.65 |

[a]BC$_a$ bootstrap interval (1000 iterations).

Criterion values and coordinates of the ROC curve [Hide]

| Criterion | Sensitivity | 95% CI | Specificity | 95% CI | +LR | 95% CI | -LR | 95% CI |
|---|---|---|---|---|---|---|---|---|
| <2.5 | 0.00 | 0.0 - 11.9 | 100.00 | 59.0 - 100.0 | | | 1.00 | 1.0 - 1.0 |
| ≤7.44 | 20.69 | 8.0 - 39.7 | 100.00 | 59.0 - 100.0 | | | 0.79 | 0.7 - 1.0 |
| ≤8.02 | 20.69 | 8.0 - 39.7 | 85.71 | 42.1 - 99.6 | 1.45 | 0.2 - 10.2 | 0.93 | 0.6 - 1.3 |
| ≤14 | 72.41 | 52.8 - 87.3 | 85.71 | 42.1 - 99.6 | 5.07 | 0.8 31.6 | 0.32 | 0.2 - 0.6 |
| ≤14.14 | 72.41 | 52.8 - 87.3 | 71.43 | 29.0 - 96.3 | 2.53 | 0.8 - 8.4 | 0.39 | 0.2 - 0.8 |
| ≤16.65 | 75.86 | 56.5 - 89.7 | 71.43 | 29.0 - 96.3 | 2.66 | 0.8 - 8.7 | 0.34 | 0.2 - 0.8 |
| ≤16.86 | 75.86 | 56.5 - 89.7 | 42.86 | 9.9 - 81.6 | 1.33 | 0.7 - 2.6 | 0.56 | 0.2 - 1.6 |
| ≤19.88 | 96.55 | 82.2 - 99.9 | 42.86 | 9.9 - 81.6 | 1.69 | 0.9 - 3.2 | 0.080 | 0.010 - 0.7 |
| ≤22.82 | 96.55 | 82.2 - 99.9 | 0.00 | 0.0 - 41.0 | 0.97 | 0.9 - 1.0 | | |
| ≤26.22 | 100.00 | 88.1 - 100.0 | 0.00 | 0.0 - 41.0 | 1.00 | 1.0 - 1.0 | | |

FIG. 6

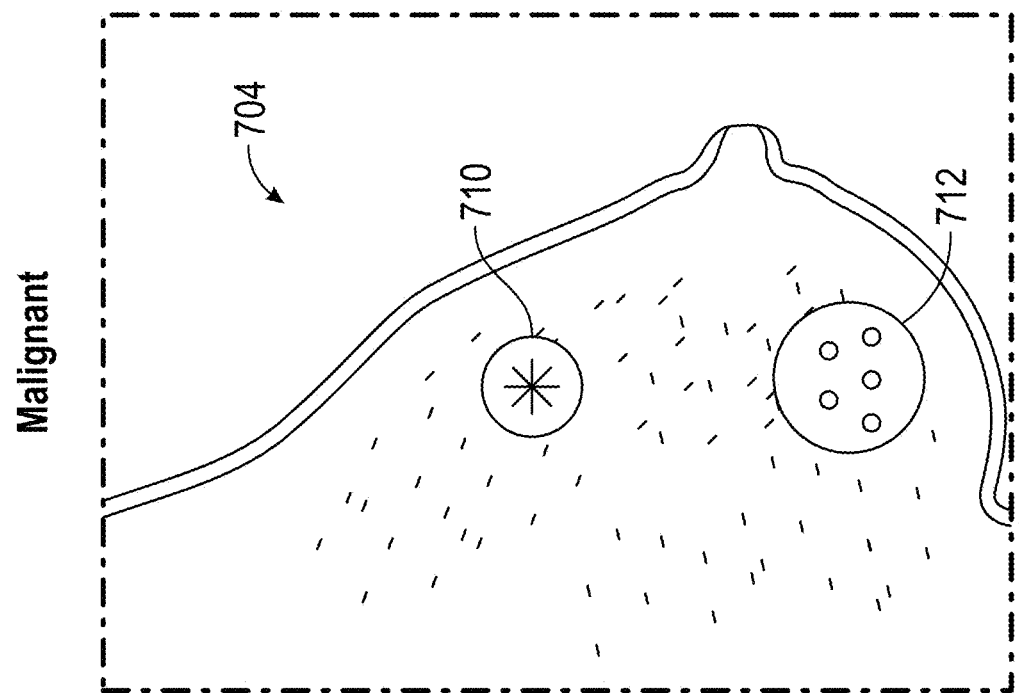
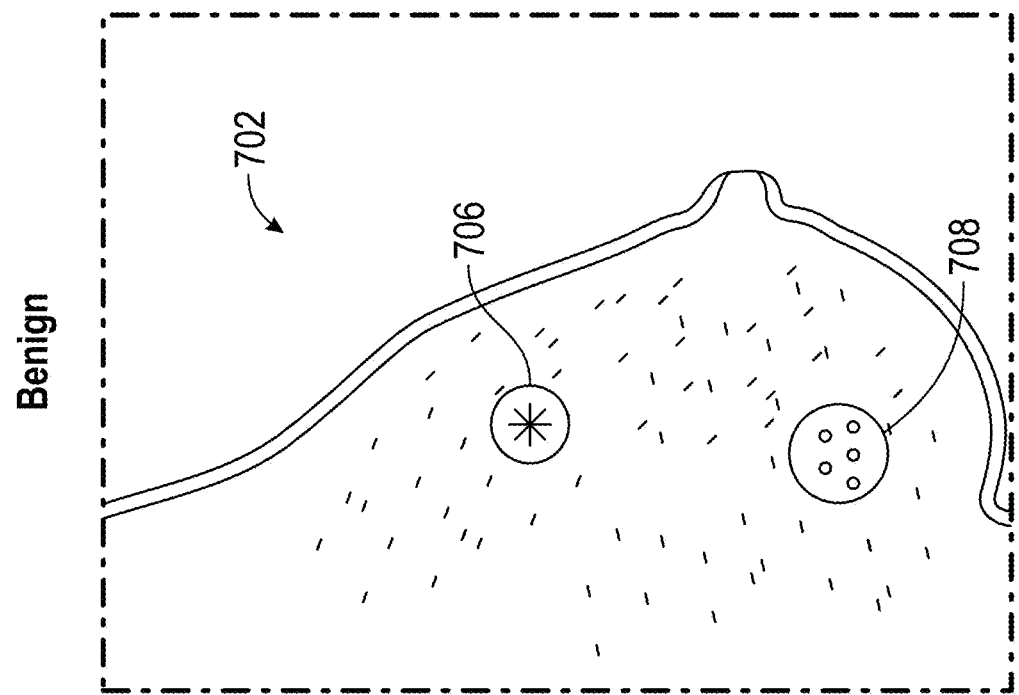
FIG. 7

SYSTEMS AND METHODS FOR RELIABLY DIAGNOSING BREAST CANCER USING QUANTITATIVE TEXTURAL ANALYSIS

TECHNICAL FIELD

The present invention relates, generally, to a biomarker signature for determining whether breast imaging data embodies malignant tumor biology and, more particularly, to systems and methods for deriving the signature using quantitative textural analysis.

BACKGROUND

The Breast Imaging Reporting and Data System (BI-RADS) and was established by the American College of Radiology as an informal scheme for assigning mammogram screenings into discrete categories of perceived severity: 0-incomplete; 1-negative; 2-benign findings; 3-probably benign; 4-suspicious abnormality; 5-highly suspicious of malignancy; and 6-known biopsy with proven malignancy. A follow-up biopsy is typically recommended for BI-RADS category 4 and higher. However, biopsies ultimately confirm that 70%-80% of BI-RADS 4 designations are benign. Consequently, many women undergo painful and expensive biopsies only to find that the tumor is benign due to the high rate of false positives.

An evolving strategy for the non-invasive interrogation of tumors involves analyzing diagnostic images to identify patterns of appearances that are linked to tumor biology. Imaging analysis provides a non-invasive, low risk approach to assessing tumor biology prior to therapy and an objective pathway for monitoring immunotherapy response.

Using signals detected on image data to characterize tumor biology is based on several factors including: (1) tumor images express underlying tumor biology; (2) growth kinetics and other drivers of oncologic transformation may have unique expression patterns on imaging; (3) unique expression patterns can manifest themselves as imaging phenotypes; and (4) the imaging phenotypes can be characterized both qualitatively and quantitatively. Thus, an understanding of disease biology can be derived, measured, inferred or predicted by examining the imaging phenotype or appearance of a tumor by different radiologic means. This coupled with imaging's ability to provide a comprehensive and real-time assessment of the entire tumor and its microenvironment make quantitative imaging an attractive tool for rapid assessment and prognosis.

Qualitative descriptions of the appearance of tumors on imaging can provide some degree of biologic characterization but are open to interpretation and lack standardization and reproducibility. Although there is general agreement on many qualitative descriptors, reader variability can be broad. Thus, being able to take qualitative features and perform quantitative analysis on imaging is appealing.

The University College in London (UCL) has developed a software platform known as TexRAD that provides quantitative measurements referred to herein as Quantitative Textural Analysis (QTA or TA) of tumor lesions based on conventional (e.g., mammographic) images. QTA as a post-processing technique can be used to quantify tissue complexity by assessing the distribution of textural features (or heterogeneity) within a tumor lesion and their change following treatment. Studies have shown that tumor complexity is seen in multiple imaging modalities and can be derived from many different image types, sequences or imaging series (e.g. CT, MRI, PET, and Mammography).

Tumor complexity can be quantified by QTA using a range of measurable parameters based on enhancement characteristics and/or density changes on a local level by clustering small groups of pixels together using filter kernels (referred to as spatial scale filters (SSF)) within a lesion itself. The output from the analysis then provides a measure of tumor heterogeneity. However, much of the heterogeneity visible on a displayed image can represent photon noise, which tends to mask or suppress the signal strength of underlying biologic information. By first filtering out the noise, QTA analysis can then be used to more effectively probe the biological diversity inherent in tumor complexity.

Notwithstanding the potential for QTA as a tool for deriving imaging biomarkers, a reliable signature for differentiating between malignant and non-malignant BIRADS 4 mammographic lesions remains elusive.

Methods and apparatus are thus needed which overcome the limitations of the prior art.

Various features and characteristics will also become apparent from the subsequent detailed description and the appended claims, taken in conjunction with the accompanying drawings and this background section.

BRIEF SUMMARY

The present invention provides a biomarker signature for determining whether a lesion identified in a breast image is malignant. The signature is derived from aggregate imaging data in conjunction with quantitative textural analysis (QTA) and logistical regression modeling techniques. Various embodiments involve: i) unambiguously identifying a first population of known malignancies and a second population of known non-malignancies; ii) processing conventional imaging (e.g., mammography) data for both populations using a quantitative textural analysis (QTA) platform; iii) generating, for both populations, respective histograms and related quantitative metrics such as mean pixel density, standard deviation of the histogram curve, mean positive pixel value of the pixels that are in the positive value range, entropy, skewness, and kurtosis of the curves; iv) performing logistical regression on the quantitative metrics for both populations to yield a model predictive signature; v) performing QTA on a subsequent breast cancer patient; vi) evaluating (e.g., comparing) one or more relevant QTA metrics for the subsequent patient against the model predictive signature; and vii) confirming or refuting the malignancy hypothesis for the subsequent patient, based on the comparison.

In an embodiment, the predictive signature is derived using Quantitative Textural Analysis (QTA) and expressed in the form $Y=XC_x+B$, where: $Y$ is a predictive indicator ranging from 0 to 1; $B$ is a constant; $C_x$ is a coefficient; and $X$ is the mean positive pixel (MPP) value associated with the breast tumor under inspection.

In an embodiment, the values of $B$ and $C_x$ are derived using a spatial scale filter (SSF) of 0.8, the value of $C_x$ is about (−0.0005), and the value of $B$ is about 0.8466.

Various other embodiments, aspects, and features are described in greater detail below.

BRIEF DESCRIPTION OF THE DRAWING FIGURES

Exemplary embodiments will hereinafter be described in conjunction with the appended drawing figures, wherein like numerals denote like elements, and:

FIGS. 3A and 3B are data matrices setting forth raw data and log regression data, respectively, for QTA derived parameters from breast cancer imaging data in accordance with various embodiments;

FIG. 6 is a table representing the data displayed in FIG. 5 in tabular form; and FIG. 7 is a schematic representation of a benign lesion image juxtaposed with a malignant lesion image, each including respective normal tissue regions of interest (ROI) in accordance with various embodiments.

DETAILED DESCRIPTION OF PREFERRED EXEMPLARY EMBODIMENTS

Figure 1:
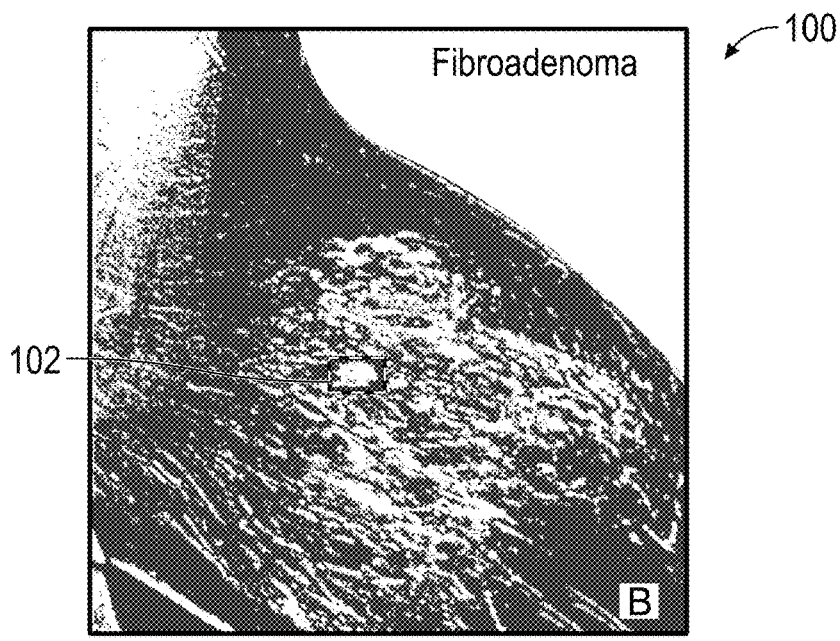
FIG. 1 is an exemplary mammography image illustrating a region of interest (ROI) embodying a lesion in accordance with various embodiments.

The following detailed description of the invention is merely exemplary in nature and is not intended to limit the invention or the application and uses of the invention. Furthermore, there is no intention to be bound by any theory presented in the preceding background or the following detailed description.

Various embodiments of the present invention relate to a biomarker signature and methods for developing a biomarker signature for distinguishing between malignant and benign breast tumors, including the steps of: i) obtaining images from CT, MRI, US, PET, DEXA, digital mammography, JPEGS, Angiography, tomosysthesis, SPECT, gamma cameras, and/or optical platforms; ii) loading the imaging data onto a suitable QTA platform (e.g., TexRAD) and selecting a region of interest (ROI) surrounding the tumor in the form of a rectangle, Ellipse, polygon, seed point, or other region encompassing the tumor; iii) selecting an appropriate filter algorithm (e.g., Mammo general, Mammo fine); iv) filtering the pixels to a single common size and shape and clustering them together as nearest neighbors into groups of 2, 3, 4, 5, and/or 6 pixels (or fractional values thereof) representing respective spatial scale filters (SSFs) ranging from 0 (no filter), 2 (fine), 3-4 (moderate), to 5-6 (coarse); v) applying the different SSFs to the ROI area pixels and generating a histograph frequency curve for each SSF; vi) deconstructing each curve to yield metrics representing, for example, mean pixel density, standard deviation of the histogram curve, mean positive pixel (mpp) values of the pixels that are in the positive value range, entropy, skewness, and kurtosis; vii) displaying the values in a matrix or otherwise representing the values in the form of equations; viii) performing logistical regression on the matrix values; and ix) using the results of the logistical regression individually or in combination with other clinical, laboratory, imaging, demographic, or other bio-informatic measurements to create imaging phenotypes for further defining a predicted outcome.

Imaging modalities such as mammography, analytical techniques such as QTA, and logistical regression algorithms are powerful tools; yet they are only tools. By themselves, they do not advance patient care. Rather, the ingenuity, creativity, commitment, and passion—in short, the inspiration and perspiration of human researchers—must ultimately be brought to bear on these technologies. The foregoing analytical tools are employed by the cancer researcher just as the chisel and rasp are used by the sculptor to coax a work of art out of a slab of marble. The present inventor has successfully employed QTA and logistical regression techniques on aggregate imaging data for unambiguously known breast cancer malignancies and unambiguously known non-malignancies to develop a statistically reliable signature for determining the presence of malignant breast cancer. Consequently, the number of breast cancer patients required to undergo unnecessary biopsies may be concomitantly reduced.

In an embodiment, image data corresponding to tumor (lesion) tissue was analyzed for two groups: i) known malignant breast tumors; and ii) known benign breast tumors. QTA revealed mean positive pixel (MPP) density and, to a lesser extent, kurtosis as significant metrics in the signature. Regression analysis confirmed that both values are important indicators of breast tumor malignancy.

More particularly, after deriving the QTA data, the data may be modeled using one or more of: i) a t-test (to confirm that the means of two population groups are statistically different from each other); ii) a Spearman correlation (a nonparametric measure of statistical dependence between two variables); and iii) an ROC analysis to yield threshold values (values above the threshold are likely to be malignant, whereas numbers below the threshold are likely benign (or vice versa)). In the context of the present invention, the foregoing yielded a bio-marker signature of the form $$1 = X(C1) + Y(C2) + B,$$

where 1 means "yes" (the tumor is malignant), X is MPP, Y is kurtosis, C1 and C2 are MPP and kurtosis coefficients, respectively, and B is a constant. Alternatively, the bio-marker signature may be expressed in terms of a single variable in the form $$1 = A(C1) + B,$$

where, A is a dependent variable such as MPP or kurtosis.

Referring now to FIG. 1, a digital mammography image 100 for each of a plurality of breast cancer tumors is analyzed. For each image, a region of interest (ROI) 102 is identified (e.g., manually or algorithmically). The pixels within each ROI 102 are processed using QTA. An initial processing step involves selecting an appropriate filter based on thresholds of density, with air being the least dense and bone being the most dense. That is, the filter seeks to remove air and bone pixels, leaving only pixels within the ROI of biological relevance.

Figure 2:
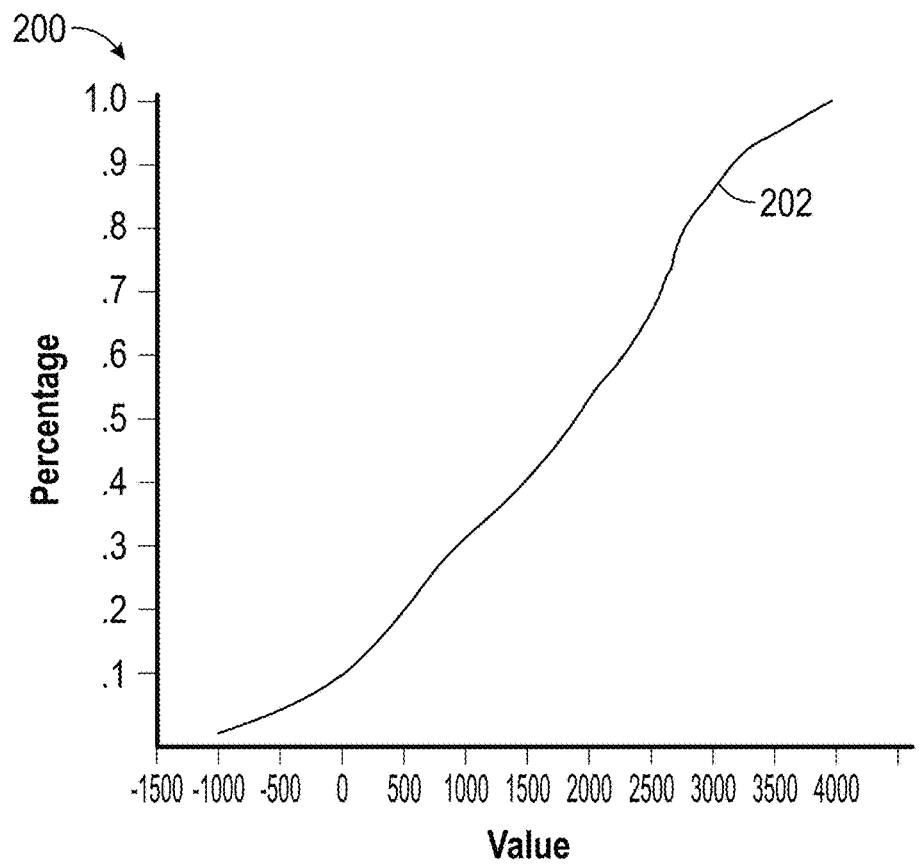
FIG. 2 is an exemplary histogram curve in accordance with various embodiments.

Referring now to FIG. 2, the QTA platform then generates a histogram 200 plotting 202 the frequency of occurrence (Y-axis) of pixels, expressed in terms of number of pixels or percentage of total pixels, for a range of pixel density values (X-axis). Radiological images typically display greyscale values in terms of Hounsfield units, where water=0 in a scale from −1500 to +1500 and above (e.g., up to 4,000 units). Pixels more dense than water are positive; pixels less dense than water have negative values. Density values may be generally grouped into four tissue types that exhibit contrast: air (less than −80); fat (−80 to −20); water/soft tissue (−20 to 300); and bone (above 300). After applying a selected band pass filter to remove the very high and very low density pixels, a histogram is generated upon which various calculations and statistical analyses are performed, as described in greater detail below.

Figure 3A:
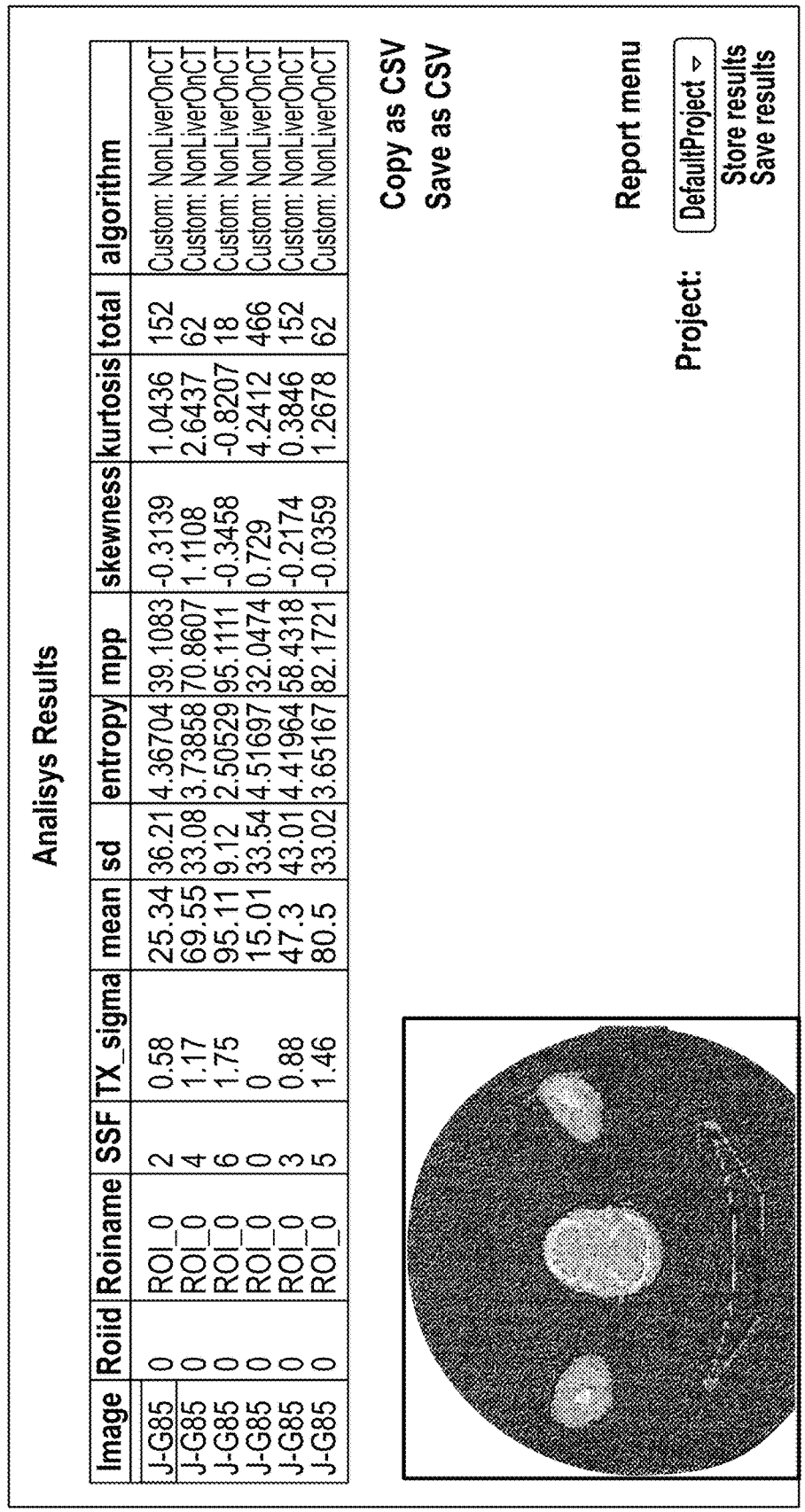

Referring now to FIGS. 3A and 3B, the system (e.g., TexRAD) then calculates various metrics (MPP data 300A is shown in FIG. 3A) for each population group (malignant and benign) using one or more spatial scale filter (SSF) filter values (SSF(0)-SSF(6)), including: i) the mean pixel value representing the average density within a cluster of pixels at a given SSF level; ii) the standard deviation (SD) which is a measure of tumor heterogeneity and microstructural change; iii) mean positive pixel (mpp) value; iv) kurtosis which is determined by the height of the histogram and regarded as a measure of tumor angiogenesis, vascular shunting and/or tumor homogeneity; v) entropy representing the mean density of clustered pixels over the entire ROI area (e.g., Ln [mean density/total pixels]) and is based on different filtering parameters that are reflective of tumor homo/heterogeneity; and vi) skewness used to measure the symmetry of contrast distribution in regions of interest, where skewness is measured by the slant of the peak either to the right (negative skewness) or to the left (positive skewness).

FIG. 3B includes data 300B representing log regression analysis of the data shown in FIG. 3A.

Figure 4:
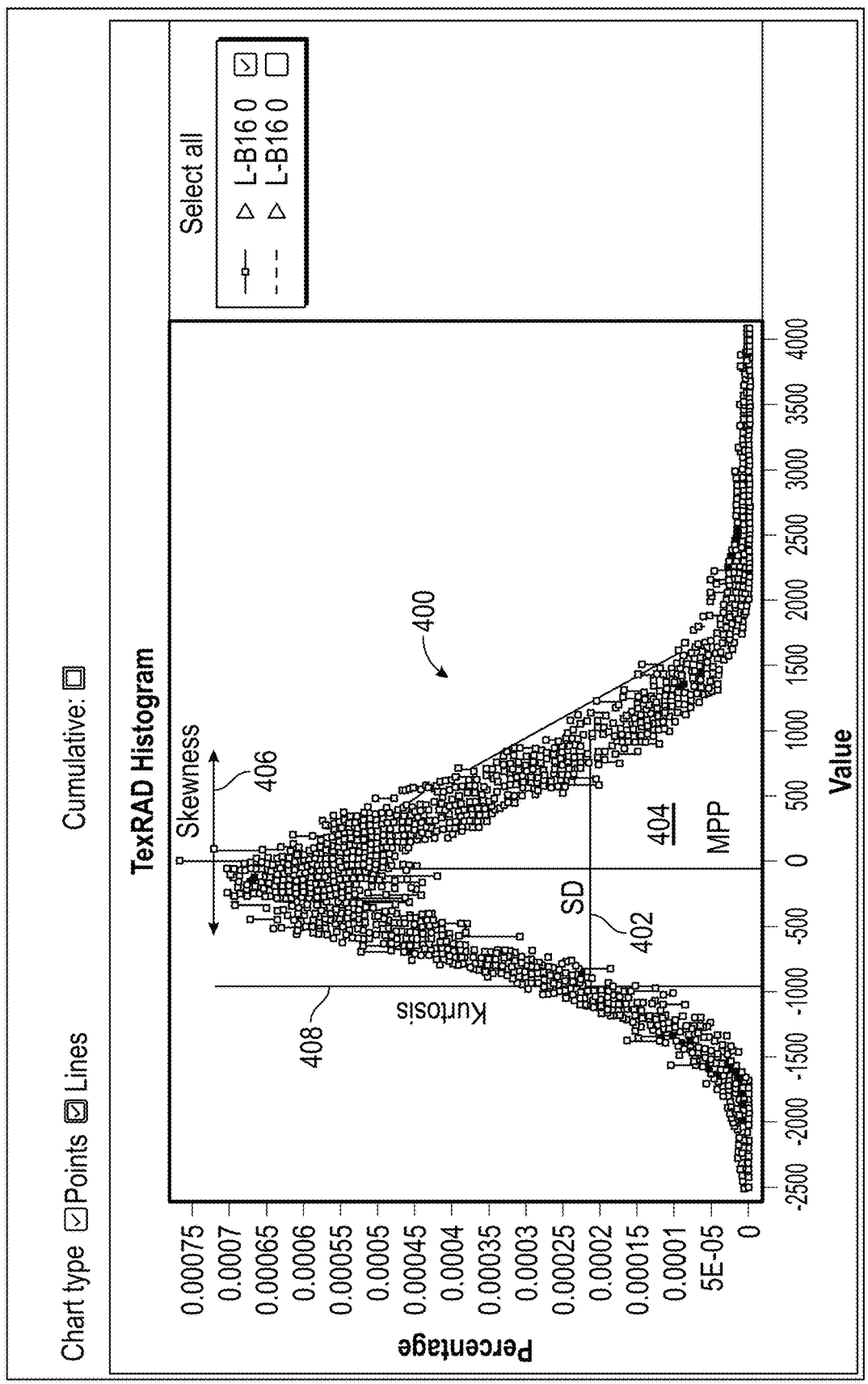
FIG. 4 is an exemplary histogram illustrating quantitative metrics in accordance with various embodiments.

The foregoing histogram and the associated metrics embody biological information, which the present inventor seeks to harness in the form of a signature useful in discriminating malignant from non-malignant BIRADS 4 and above breast tumor designations. Specifically, the present inventor seeks to characterize the data in terms of a signature against which future breast cancer patient scans may be evaluated to confirm or refute the malignancy diagnosis with a high degree of confidence. FIG. 4 illustrates a histogram 400 and graphically depicts the following exemplary metrics: standard deviation 402; MPP 404; skewness 406; and kurtosis 408.

The foregoing metrics may then be processed using a simple T-test to determine whether a difference between respective mean values for the two population groups (e.g., malignant and benign) results from inherent randomness in sample selection. Each metric which exhibits a significant difference between the malignant population and the benign population is a good candidate for including in the signature.

A more robust signature may be derived using logistical regression to yield a signature representative of the underlying biology, where metrics which influence the outcome (malignant versus benign) are preserved in the model, and where metrics which do not influence the outcome are not preserved in the model. More particularly, known malignant images are allocated a 1 and known benign images are allocated a zero, where zero and 1 are the dependent variables in the logistical regression analysis. The logistical regression model then reveals the principal factors that align with malignant and benign tumors, as well as their coefficients. This can be done using forward, backward, step wise, or any other desired statistical protocol.

In an embodiment, the logistical regression analysis employs a matrix of equations of the form $1=Ax_1+Bx_2+Cx_3+Dx_4+Ex_5+Fx_6$ for malignant tumors, and of the form $0=Ax_1+Bx_2+Cx_3+Dx_4+Ex_5+Fx_6$ for benign tumors, where $x_1$ corresponds to the mean, $x_2$ corresponds to the standard deviation, $x_3$ corresponds to entropy, $x_4$ corresponds to MPP, $x_5$ corresponds to skewness, and $x_6$ corresponds to kurtosis. The logistical regression analysis then determines which metrics differentiate between the malignant and benign populations, and calculates the associated coefficients (e.g., A-F) for the metrics retained in the model.

In an alternate embodiment, one or more extra columns may be used in addition to the aforementioned metrics to enhance the predictive value of the signature. This additional column or columns may relate to bio-informatic metrics such as, for example, smoking history, gene mutation load, tumor markers, pathology information (age, gender), and menopausal state; logistical regression analysis may then be performed on all columns.

The logistical regression process, which may be implemented algorithmically, produces a master equation using well known techniques, and retains the statistically important independent variable or variables and discards the statistically unimportant independent variables. A binary logistic model may be used to estimate the probability of a binary response based on one or more predictor (or independent) variables (features).

Figure 5:
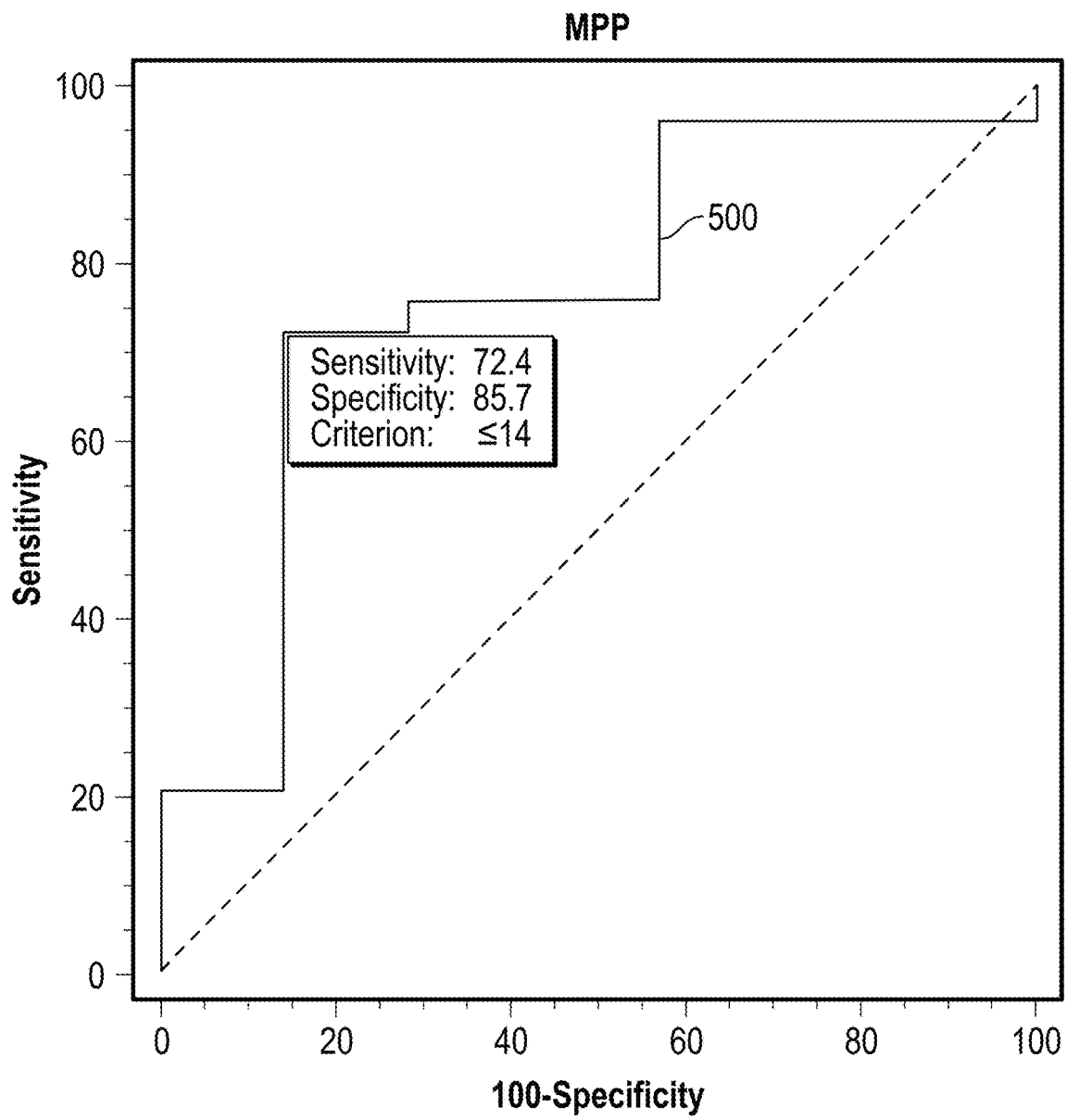
FIG. 5 is an exemplary receiver operator characteristics (ROC) curve in accordance with various embodiments.

Once a preliminary logistical regression analysis has been performed and one or more metrics are identified as significant, they may be expressed as an equation of the form $1=Ax+By+Cz$, where x, y, and z are the metrics determined to be linked to the malignant versus benign outcome, and A, B, and C are their corresponding coefficients (at least one of which is non-zero). With momentary reference to FIG. 5, this equation may then be expressed as a receiver operator characteristics (ROC) curve 500 and analyzed to determine the cut-off value which yields the highest sensitivity. For example, by inspecting an exemplary receiver operator characteristics curve, one may conclude that if x, y, and/or z exceed predetermined threshold values, the tumor is statistically likely to be malignant. FIG. 6 is a table 600 setting forth some of the data supporting the ROC curve of FIG. 5.

Once a linkage is established between malignancy and the metrics retained in the logistical regression model, the linkage is preferably validated before declaring the signature statistically stable. That is, if a new breast image is determined to be malignant based on comparison of that image's metrics to the signature, a biopsy is then performed to confirm the malignant diagnosis. If the biopsy refutes the diagnosis (the tumor is in fact benign), the reasons underlying the discrepancy are addressed or the signature revised. Once the signature is positively validated, the validated signature becomes the predictive test which is known to a statistical certainty that declared malignancies are in fact malignant.

Referring again to FIG. 3, the results of logistical regression analyses suggest that a spatial scale frequency (SSF) filter level of 0.8 was more statistically significant than other SSF levels differentiating malignant from benign breast tumors. The signature resulting from the logistical regression analysis retained the MPP and kurtosis values as significant; the remaining metrics (mean, standard deviation, entropy, and skewness) were not retained in the model. The resulting signature may thus be expressed as $1=C1(X)+B$, where X corresponds to the MPP value for a breast image under inspection, $C_1$ is a coefficient having a value in the range of (−0.0001) to (−0.001), and preferably about (−0.0005002), and B is a constant in the range of 0.5 to 0.95, and preferably about 0.8466

In an alternate embodiment, kurtosis was also retained in the model. The resulting signature may thus be expressed as $1=C1(X)+C2(Y)+B$, where X corresponds to MPP and Y corresponds to kurtosis, and $C_1$ and $C_2$ are their respective coefficients.

The foregoing equations suggest that malignancy is highly sensitive to the mean positive pixel density and, to a lesser extent, the kurtosis of the TexRAD histogram of the pixels within the region of interest for breast tumors.

In various embodiments, it may be desirable to bias the logistical regression analysis in the direction of malignancy, for example, by using a greater number of malignant image data sets scans than benign data sets. That is, since one objective is to positively identify a malignant signature, it is appropriate to bias the data to tend towards malignancy, or else the linkage between malignancy and the metrics influencing malignancy may be suppressed or washed out entirely. In various embodiments, the data set may comprise a ratio of malignant images to benign images in the range of 1:1 to 2:1.

The manner in which the malignant population and the benign population are defined will now be described in accordance with various embodiments. After evaluating the pixels within an ROI for an image (or group of images) associated with a particular patient, a follow-up biopsy is undertaken for all BIRADS 4 (and higher, if desired) diagnoses. Based on the biopsy results, it may be conclusively determined whether the tumor is malignant or benign, and the underlying image assigned to the corresponding population group (malignant or benign).

The present inventor has further determined that analyzing a normal tissue ROI (in addition to a tumor ROI) for each of a plurality of images can enhance the confidence level of the resulting signature. That is, if the underlying biology in normal tissue is also different for the malignant and benign images, one can attribute the results to factors other than the differences between malignant tumor biology and benign tumor biology. To avoid this ambiguity, an alternative embodiment analyzes data for normal tissue in both patient groups (malignant and benign cancers) to enhance the reliability of the results.

More particularly, FIG. 7 depicts a benign image 702 and a malignant image 704. The benign image includes a tumor tissue ROI 706 and a normal tissue ROI 708; the malignant image includes a tumor tissue ROI 710 and a normal tissue ROI 712. If there are no significant differences in the QTA metrics for normal (non-tumor) breast tissue between the malignant and benign patient groups, this suggests that the lesion biology itself accounts for the differences in QTA metrics between the two populations, as opposed to something in the background that was common to both lesion tissue and normal tissue in both patient groups. That is, the normal tissue from both groups functions as a statistical reference, which should be the same in both groups (since it is not tumor tissue).

In an embodiment, the QTA parameter values for the normal tissue may be subtracted from the QTA parameter values for the tumor tissue (for both populations), reasoning that the result should isolate the tumor biology (sans the common background tissue biology).

While the present invention has been described in the context of the foregoing embodiments, it will be appreciated that the invention is not so limited. For example, the various geometric features and chemistries may be adjusted to accommodate additional applications based on the teachings of the present invention.

A biomarker signature is thus provided for use in predicting breast tumor malignancy by comparing imaging data for the breast tumor to the signature, the signature is derived using Quantitative Textural Analysis (QTA) and expressed in the form $Y=XCx+B$, where: Y is a predictive indicator ranging from 0 to 1; B is a constant; Cx is a coefficient; and X is the mean positive pixel (MPP) value associated with the breast tumor under inspection.

In an embodiment, the values of B and Cx are derived using a spatial scale filter (SSF) in the range of 0.5 to 1.

In an embodiment, the values of B and Cx are derived using a spatial scale filter (SSF) of 0.8.

In an embodiment, the value of Cx is in the range of (−0.0001) to (−0.001).

In an embodiment, the value of Cx is about (−0.0005).

In an embodiment, the value of B is in the range of 0.5 to 1.

In an embodiment, the value of B is about 0.8466.

In an embodiment, mean positive pixel density is derived from imaging data associated with a subjectively determined region of interest (ROI) surrounding a breast lesion.

In an embodiment, mean positive pixel density is a measure of the average positive pixel density within a cluster of pixels derived from imaging data surrounding a tumor.

In an embodiment, the imaging data comprises one of CT scan data, MRI, US, PET, DEXA, digital mammography, JPEGS, Angiography, SPECT, and gamma camera data.

In an embodiment, the signature is derived using logistical regression analysis on a first population of known malignant breast tumor images and a second population of known benign breast tumor images.

A biomarker signature is also provided for determining whether breast tumor image data contemplates malignant biology, The signature is derived using Quantitative Textural Analysis (QTA) and expressed in the form $Y=XCx+YCy+B$, where: B is a constant; X is the mean positive pixel (MPP) value and Y is the kurtosis value for a breast tumor image under inspection; and Cx and Cy are the MPP and kurtosis coefficients, respectively.

In an embodiment, the MPP and kurtosis values are derived from imaging data associated with a cluster of pixels within a subjectively determined region of interest (ROI) surrounding a breast lesion.

A method is also provided for evaluating whether a breast tumor is malignant. The method includes: identifying a first set of malignant breast tumor images and a second set of benign breast tumor images; processing the first and second image sets using quantitative textural analysis (QTA); generating, for each member of the first and second image sets, quantitative metrics using the QTA; performing logistical regression on the quantitative metrics for the first and second sets to yield a predictive signature expressed in the form of $Y=Mx+B$ where x is the mean positive pixel value; performing QTA on a breast tumor image set for a subsequent patient; comparing the predictive signature to one or more relevant metrics associated with the subsequent patient; and declaring the breast tumor either malignant or benign for the subsequent patient based on the comparison.

In an embodiment, the imaging data comprises mammography data; Y is a predictive indicator ranging from 0 to 1; B is a constant having a value in the range of about 0.5 to 1; and M is a coefficient in the range of (−0.0001) to (−0.001).

In an embodiment, the step of processing comprises using a spatial scale filter (SSF) of about 0.8.

In an embodiment, B is a constant having a value in the range of about 0.8466; and M is a coefficient having a value in the range of about (−0.0005).

In an embodiment, the step of performing logistical regression comprises factoring in at least one of the following metrics: smoking history, gene mutation load, tumor markers, and patient age.

In an embodiment, the step of generating quantitative metrics comprises determining values for mean pixel density, standard deviation of a histogram curve, mean positive pixel value of the pixels that are in the positive value range, entropy, skewness, and kurtosis.

In an embodiment, the method also includes: identifying a first normal region of interest (ROI) surrounding normal tissue within at least one of the malignant breast tumor images; identifying a second normal ROI surrounding normal tissue within at least one of the benign breast tumor images; processing the first and second ROIs using quantitative textural analysis (QTA); generating, for the first and second ROIs, respective quantitative metrics using the QTA; calculating a first difference between i) one of the quantitative metrics associated with the first image set and ii) one of the quantitative metrics associated with the first normal ROI; calculating a second difference between i) one of the quantitative metrics associated with the second image set and ii) one of the quantitative metrics associated with the second normal ROI; and using the first and second differences to isolate malignant tumor biology.

Computer code stored in a non-transient medium is also provided which, when executed by a computer processor, performs the steps of: i) processing imaging data for a first population of malignant breast tumor images and a second population of benign breast tumor images using quantitative textural analysis (QTA); ii) generating, for each member of both populations, quantitative metrics using the QTA; iii) performing logistical regression on the quantitative metrics using the equation $1=Ax1+Bx2+Cx3+Dx4+Ex5+Fx6$ for the malignant population, and the equation $0=Ax1+Bx2+Cx3+Dx4+Ex5+Fx6$ for the benign population, where x1 corresponds to the mean, x2 corresponds to the standard deviation, x3 corresponds to entropy, x4 corresponds to MPP, x5 corresponds to skewness, and x6 corresponds to kurtosis; and iv) deriving, from the logistical regression analysis, a predictive signature of the form $Y=Mx+B$ for comparison with a breast tumor image under inspection. In the signature, B is a constant, M is a coefficient, and x corresponds to mean positive pixel density associated with the breast tumor image under inspection.

As used herein, the word "exemplary" means "serving as an example, instance, or illustration." Any implementation described herein as "exemplary" is not necessarily to be construed as preferred or advantageous over other implementations, nor is it intended to be construed as a model that must be literally duplicated.

While the foregoing detailed description will provide those skilled in the art with a convenient road map for implementing various embodiments of the invention, it should be appreciated that the particular embodiments described above are only examples, and are not intended to limit the scope, applicability, or configuration of the invention in any way. To the contrary, various changes may be made in the function and arrangement of elements described without departing from the scope of the invention.

The invention claimed is:

1. A method of evaluating whether a breast tumor is malignant, comprising the steps of:
identifying a first set of malignant breast tumor images and a second set of benign breast tumor images, each comprising mammography data;
processing the first and second image sets using quantitative textural analysis (QTA) using a spatial scale filter (SSF) of about 0.8;
generating, for each member of the first and second image sets, quantitative metrics using the QTA;
performing logistical regression on the quantitative metrics for the first and second sets to yield a predictive signature expressed in the form of $Y=Mx+B$, where x is the mean positive pixel value (MPP), Y is a predictive indicator ranging from 0.0 to 1.0, B is a constant having a value of about 0.8466, M is a coefficient having a value of about −0.0005, and the MPP is calculated using a pixel value scale that includes both negative and positive values, wherein the logistical regression includes factoring in at least one of smoking history, gene mutation load, tumor markers, and patient age;
performing QTA on a breast tumor image set for a subsequent patient
comparing the predictive signature to one or more relevant metrics associated with the subsequent patient; and
declaring the breast tumor either malignant or benign for the subsequent patient based on the comparison;
further including:
identifying a first normal region of interest (ROI) surrounding normal tissue within at least one of the malignant breast tumor images;
identifying a second normal ROI surrounding normal tissue within at least one of the benign breast tumor images;
processing the first and second ROIs using quantitative textural analysis (QTA);
generating, for the first and second ROIs, respective quantitative metrics using the QTA;
calculating a first difference between i) one of the quantitative metrics associated with the first image set and ii) one of the quantitative metrics associated with the first normal ROI;
calculating a second difference between i) one of the quantitative metrics associated with the second image set and ii) one of the quantitative metrics associated with the second normal ROI; and
using the first and second differences to isolate malignant tumor biology.

2. The method of claim 1, wherein the mean positive pixel density is derived from imaging data associated with at least one of the ROIs.

3. The method of claim 2, wherein the mean positive pixel density is a measure of an average positive pixel density within a cluster of pixels derived from imaging data surrounding a tumor.

4. The method of claim 2, wherein the imaging data comprises one of CT scan data, Mill, US, PET, DEXA, digital mammography, JPEGs, angiography, SPECT, and gamma camera data.

5. A biomarker signature system for predicting whether a breast tumor is malignant, comprising: an imaging platform configured to acquire a first set of malignant breast tumor images and a second set of benign breast tumor images, each comprising mammography data; a storage system configured to store the first set of malignant breastumor images and the second set of benign breast tumor images; a processor configured to execute machine-readable software instructions configured to cause the processor to: process the first an d second image sets using quantitative textural analysis (QTA) using a spatial scale filter (SSF) of about 0.8; generate, for each member of the first and second image sets, quantitative metrics using the QTA; perform logistical regression on the quantitative metrics for the first and second sets to yield a predictive signature expressed in the form of $Y=Mx+B$, where x is the mean positive pixel value (MPP), Y is a predictive indicator ranging from 0.0 to 1.0, B is a constant having a value of about 0.8466, M is a coefficient having a value of about −0.0005, and the MPP is calculated using a pixel value scale that includes both negative and positive values, wherein the logistical regression includes factoring in at least one of smoking history, gene mutation load, tumor markers, and patient age; perform QTA on a breast tumor image set for a subsequentpatient; compare the predictive signature to one or more relevant metrics associated with the subsequentpatient; and declare the breast tumor either malignant or benign for the subsequent patient based on the comparison; identify a first normal region of interest (ROI) surroundingnormal tissue within at least one of the malignant breasttumor images; identify a second normal ROI surrounding normal tissue within at least one of the benign breast tumor images; process the first and second ROIs using quantitative textural analysis (QTA); generate, for the first and second ROIs, respective quantitative metrics using the QTA; calculate a first difference between i) one of the quantitative metrics associated with the first image set and ii) one of the quantitative metrics associated with the first normal ROI; calculate a second difference between i) one of the quantitative metrics associated with the second image set and ii) one of the quantitative metrics associated with the second normal ROI; and use the first and second differences to isolate malignant tumor biology.

6. The system of claim 5, wherein the mean positive pixel density is a measure of an average positive pixel density within a cluster of pixels derived from imaging data surrounding a tumor.

7. The system of claim 5, wherein the imaging data comprises one of CT scan data, MRI, US, PET, DEXA, digital mammography, JPEGs, angiography, SPECT, and gamma camera data.

* * * * *